United States Patent [19]

Tsuge et al.

[11] Patent Number: 5,496,943
[45] Date of Patent: Mar. 5, 1996

[54] HETEROCYCLIC COMPOUNDS AND THEIR PRODUCTION

[75] Inventors: Otohiko Tsuge, Fukuoka; Taizo Hatta, Kumamoto; Satoshi Urano, Tsuzuki; Noriyuki Tsuboniwa, Higashiosaka; Ryuzo Mizuguchi, Yawata, all of Japan

[73] Assignee: Nippon Paint Co., Ltd., Osaka, Japan

[21] Appl. No.: 850,914

[22] Filed: Mar. 13, 1992

[30] Foreign Application Priority Data

Mar. 14, 1991 [JP] Japan .................................. 3-049906

[51] Int. Cl.⁶ ...................... C07D 265/06; C07D 265/10; C07D 309/32; C07D 211/40
[52] U.S. Cl. ................... 544/97; 544/96; 544/69; 544/72; 544/71; 544/78; 544/82; 544/66; 544/63; 544/130; 544/149; 546/220; 546/208; 546/243; 546/14; 546/16; 549/214; 549/414; 549/415; 549/416; 549/417; 549/419; 549/424; 540/456; 540/487; 540/490; 540/489
[58] Field of Search ................... 544/97, 96, 69, 544/72, 71, 78, 82, 66, 63, 130, 149; 546/220, 14; 549/214, 416, 424; 540/456, 489

[56] References Cited

U.S. PATENT DOCUMENTS 3,634,406  1/1972  Doumaux ................. 540/526

FOREIGN PATENT DOCUMENTS

| | | |
|---|---|---|
| 0105665 | 9/1982 | European Pat. Off. . |
| 0143613 | 6/1985 | European Pat. Off. . |
| 0223335 | 8/1986 | European Pat. Off. . |
| 0207621 | 1/1987 | European Pat. Off. . |
| 0243207 | 10/1987 | European Pat. Off. . |
| 0449488 | 3/1991 | European Pat. Off. . |
| 1531313 | 6/1985 | France . |
| 2143234 | 2/1985 | United Kingdom . |

OTHER PUBLICATIONS

Tetrahedron Letters, vol. 26, No. 10, 1985, pp. 1311–1314; Corriu, et al.; "1–4–Addition Reactions to Methacrylaminds: A one Pot Synthesis . . . ".

Tetrahedron Letters, vol. 42, No. 8, 1986, pp. 2293–2301, Chuit, et al.; "Reaction de Michael Sur Des Amids Alpha, Beta Insatures Activees . . . ".

*Primary Examiner*—John M. Ford
*Attorney, Agent, or Firm*—Townsend & Banta

[57] ABSTRACT

Disclosed is a novel heterocyclic compound selected from the group consisting of the compounds [IV] to [VII], [IX] and [X]. The heterocyclic compound is useful for reactive materials in chemical industry. A process for producing the heterocyclic compound is also disclosed.

5 Claims, No Drawings

HETEROCYCLIC COMPOUNDS AND THEIR PRODUCTION

FIELD OF THE INVENTION

The present invention relates to novel heterocyclic compounds and their production.

BACKGROUND OF THE INVENTION

Compounds containing an isocyanate group have widely been used in the field of polymer chemistry because of their excellent reactivities. Particularly, compounds containing both a polymeric carbon-carbon unsaturated group and an isocyanate group in the same molecule can be used for a wide variety of industrial fields because each functional group respectively contributes to various reactions in different reaction mechanism. By paying attention to such an usefulness, the present inventors have already provided an acylisocyanate compound represented by the formula:

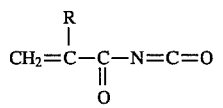

[wherein R is a lower alkyl group] (U.S. Pat. No. 4,925,982).

The above acylisocyanate compound [I] is generally liquid which is stable at a normal temperature and is easily handled. Further, it contains a polymeric carbon-carbon unsaturated group and an isocyanate group in a molecule and a carbonyl group is also present between both functional groups while adjoining them and, therefore, activity of the carbon-carbon unsaturated group as well as that of the isocyanate group are enhanced. Thus, it is in such a state that various addition reactions can be conducted. Namely, various reactions (e.g. radical polymerization, anion polymerization, dimerization, trimerization, polarity addition, active hydrogen addition, etc.) based on the part A (conjugated double bond) and part B (acylisocyanate group) of the following formula:

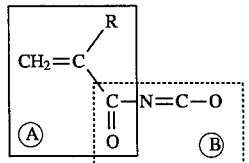

[wherein R is as defined above] can be conducted by the acylisocyanate compound [I].

Accordingly, it is expected that the acylisocyanate compound [I] is widely used in chemical industry as reactive materials.

For example, the present inventors have already disclosed that a compound represented by the formula:

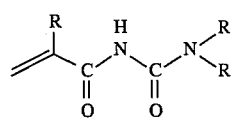

[wherein each R is the same or different and is as defined above] (Japanese Patent Kokai No. 60-231644 corresponding to U.S. Pat. No. 4,935,413) and a compound represented by the formula:

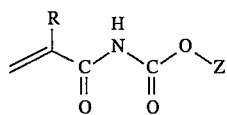

[wherein R is as defined above, and Z is an organic group containing a tertiary amino group] (Japanese Patent Kokai No. 61-17554 corresponding U.S. Pat. No. 4,935,413) are useful in the fields of coatings, plastics and the like.

Under these circumstances, the present inventors have found that the diene structure part B (acylisocyanate group) containing a hetero atom in the acylisocyanate compound (I) makes a cyclic addition reaction with a suitable dienophile to form a novel heterocyclic compound, and the above heterocyclic compound can further make a cyclic addition reaction with the suitable dienophile to form an additional novel heterocyclic compound, and the present invention has been completed.

OBJECTS OF THE INVENTION

The main object of the present invention is to provide novel heterocyclic compounds useful for reactive materials in chemical industry.

This object as well as other objects and advantages of the present invention will become apparent to those skilled in the art from the following description.

SUMMARY OF THE INVENTION

According to the present invention, there is provided the heterocyclic compounds [IV] to [VII], [IX] and [X] represented by the following formulas:

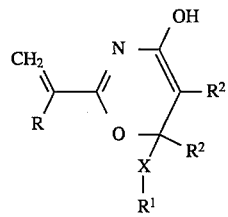

[wherein R is as defined above; $R^1$ is an alkyl, aryl, aralkyl, alkenyl or alkynyl group; each $R^2$ is the same or different and respectively indicates —H, —$R^1$, —$OR^1$, —$CONR_2^1$, —$CONHR^1$, —CHO, —$COR^1$, —$CO_2R^1$, —$NO_2$ or halogen atom, or $R^1$ and $R^2$ may bond together with or without O or N atom to form a cyclic group;

X is

—O—, —S—, or

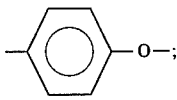

two substituents —$R^1$ on N atom is the same or different when X is

and they may bond together with or without O or N atom to form a cyclic group; and the above substituents $R^1$ and $R^2$ may be substituted],

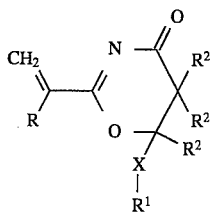
[V]

[wherein R, $R^1$ $R^2$ and X are as defined above],

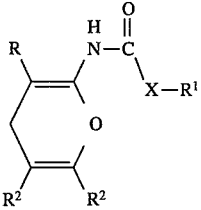
[VI]

[wherein R, $R^1$, $R^2$ and X are as defined above],

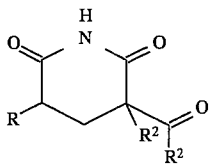
[VII]

[wherein R and $R^2$ are as defined above],

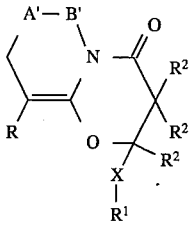
[IX]

[wherein —A'—B'— is a reactive residue of A'=B' as defined below, and R, $R^1$, $R^2$ and X are as defined above], and

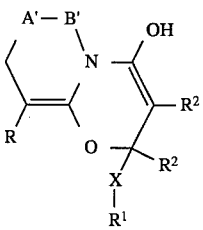
[X]

[wherein —A'—B'— is a reactive residue of A'=B' as defined below, and R, $R^1$, $R^2$ and X are as defined above].

The present invention also provides a process for producing the hydrocyclic compounds [IV] to [VII], [IX] and [X].

DETAILED EXPLANATION OF THE INVENTION

In the above formulas, R is a lower alkyl group and examples thereof include those having 1 to 6 carbon atoms.

The substituent represented by $R^1$ may be, for example, alkyl, aryl, aralkyl, alkenyl or alkynyl group. Examples of the alkyl group include those which are described as to the above substituent R, examples of the aryl group include phenyl group, naphthyl group, etc., examples of the aralkyl group include benzyl group, phenethyl group, etc., examples of the aryl group include allyl group, etc., and examples of the alkynyl group include propargyl group and the like.

X is a substituent represented by the formula:

[XII]

[wherein $R^1$ is as defined above], —O—, —S— or

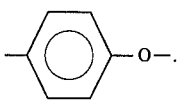

Further, when X is a group of the formula [XII], —X—$R^1$ is

[wherein $R^1$ is as defined above], but two substituents are the same or different. Further, these two substituents $R^1$ may bond together with or without O or N atom to form a cyclic group.

The above substituents $R^1$ and $R^2$ may be substituted with a suitable substituent. The suitable substituent may be, for example, aliphatic group, aromatic group, alicyclic group, hetero substituent and the like. Examples of the aliphatic group include alkyl group (e.g. methyl, ethyl, propyl, butyl, etc.), alkenyl group (e.g. vinyl, allyl, etc.), aralkyl group (e.g. benzyl, etc.), alkynyl group (e.g. ethynyl, propargyl, etc.) and the like. Examples of the aromatic group include aryl group (e.g. phenyl, naphthyl, etc.) and the like. Examples of the alicyclic group include cyclopropyl, cyclopentyl, cyclohexyl and the like. Examples of the hetero substituent include alkoxy group, halogen atom, acyl group, ester group, nitro group, cyano group, sulfide group, sulfone group, tertiary amino group, silicon and the like.

The compounds [IV] to [VII] of the present invention can be selectively obtained as a mixture by reacting the compound [I] with the compound of the formula:

$$A=B \quad [II]$$

As the the compound [I], for example, there are methacryloyl isocyanate, acryloyl isocyanate and the like.

As the compound [II], for example, there are vinyl ethers, enamines, vinyl thioethers, alkoxyalkynes, thioalkoxyalkynes, ynamines, N-substituted maleimides, maleic anhydride, maleic acid and esters thereof, fumaric acid and esters thereof, acetylenemonocarboxylic acids and esters thereof, acetylenedicarboxylic acids and esters thereof, phenylacetylenes, acylated acetylenes, (meth)acrylic acid and esters thereof, (meth)acrylonitrile, quinones, cyanoethylenes, isocyanates, ketenes, ketenimines, carbodiimides, thioketenes, sulfinylimines, ketones, isocyanides, carbenes, allenes, isothiocyanates, sulfines, carbon bisulfide, sulfondiimides, azomethine compounds, nitriles, oxiranes, nitrons, nitrile oxides, thiiranes and azirines, and it may be substituted or have a cyclic structure.

For example, the above compound [II] may be a compound represented by the formula:

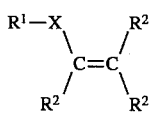

[wherein R, $R^1$, $R^2$ and X are as defined above].

As the compound [III], for example, there are 1-pyrrolidino-1-phenylenamine, ethyl vinyl ether, methyl vinyl ether, butyl vinyl ether, isobutyl vinyl ether, 2-chloromethyl vinyl ether, 4-vinylanisole, ketene acetal, phenylvinylz sulfide, 2-vinyl thioethyl acetate, 1-piperidino isobutene, 1-dimethylamino-2-nitroethylene, 3-aminocrotonate, 1-acetyl-2-methylaminopropane, 1-acetyl-2-anilinopropene, ethyl-β-dimethylaminocronate, 2-morpholino- 2-butene, 2-morpholino-2-pentene, 1,2-dimethoxycarbonyl-1-aziridinoethylene, ethyl-β-dimethylaminoacrylate, 4-(N,N-diethylamino)- 4-phenyl-3-butenenitrile, N,N-dimethylvinyl amine, N-methyl-N-propenyl aniline, 1-chloro-N,N-dimethylpropenylaniline and the like.

Further, the compound [III] may be those in which $R^1$ and $R^2$ as well as the other substituent (e.g. the other $R^2$, etc.) bond together with O, N or S atom to form a cyclic group. For example, the compound [III] may be a compound represented by the formula:

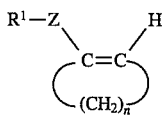

[wherein —$(CH_2)_n$— is a methylene chain in which O, N or S atom may be present in a chain, which may have a substituent or have a fused ring structure; n is an integer of 2 to 20; and R and X are as defined above].

In the above compound [XIII], a cyclic methylene chain may have a substituent, or fused with the other ring. As the above substituent, for example, there are alkyl group (e.g. methyl ethyl, etc.), aryl group (e.g. phenyl group, etc.) and the like. Further, as the other ring, for example, there are aromatic ring (e.g. benzene ring, etc.). Examples of the above compound [XIII] include 5,6-dihydro-4-methoxy-2H-pyran, morpholinocyclohexane, pyrrolidinoindene, morpholinocyclopentene, morpholinodihydrothiophene, 1-methyl-2-phenyl-1-azacycloheptane, N-methyl-2-phenylpyrroline, N-methyl-2-butylpyrroline, N-methyl-2-ethylpyrroline, N-methyl-2-[6'-methoxynaphthyl-( 2')] pyridine, pyrrolidinocyclohexene, pyrrolidinocyclopentene, pyrrolidinocycloheptane, pyrrolidinocyclooctene, pyrrolidino2-methylcycloheptene, pyrrolidinocyclooctene, pyrrolidino2-methylcyclohexene, pyrrolidino2-phenylcyclohexene, pyrrolidinocyclononene and the like.

In the case of the above reaction, if necessary, a catalyst may be added. Further, the above reaction may be conducted in the absence or presence of an inert solvent. As the inert solvent, for example, there are aliphatic hydrocarbons (e.g. pentane, hexane, etc.), aromatic hydrocarbons (e.g. benzene, toluene, xylene, etc.), alicyclic hydrocarbons (e.g. cyclohexane, cyclopentane, etc.), halogenated hydrocarbons (e.g. chloroform, dichloromethane, dichlorobenzene, bromobenzene, etc.), ketones (e.g. acetone, methyl ethyl ketone (MEK), cyclohexane, etc.), esters (e.g. ethyl acetate, butyl acetate, etc.), ethers (e.g. diethyl ether, dioxane, diisopropyl ether, anisole, diphenyl ether, etc.), nitriles (e.g. acetonitrile, benzonitrile, etc.), amides (e.g. dimethylformamide, N-methylpyrrolidone, etc.), nitrobenzene, dimethylsulfoxide and the like.

The reaction composition may be essentially based on a stoichiometric ratio, for example, the reaction is conducted using 1 to 30 molar equivalent of the compound [III]. The reaction is normally conducted by mixing with stirring at −20° to 200° C. Thereafter, if necessary, the solvent is distilled off and filtered, and then a normal refining operation (e.g. recrystallization, column chromatography, etc.) is conducted to obtain novel compounds [IV] to [VII] of the present invention.

Among them, the compounds [IV] and [V] have the diene part ($CH_2$=C—C=N) in a molecule and, therefore, they further react with a compound represented by the formula:

$$A'\!=\!B' \qquad [VIII]$$

to produce an additional novel heterocyclic compound [IX] or [X].

As the above compound [VIII], for example, there are N-substituted maleimides, maleic anhydride, maleic acid and esters thereof, fumaric acid and esters thereof, acetylenemonocarboxylic acid and esters thereof, acetylenedicarboxylic acid and esters thereof, phenylacetylenes, acylated acetylenes, (meth)acrylic acid and esters thereof, (meth)acrylonitrile, quinones, cyanoethylenes and the like.

For example, the compound [VIII] may be a compound represented by the formula:

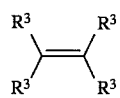

[wherein each $R^3$ is the same or different and respectively indicates —$R^2$—$CO_2H$ or —CN, or

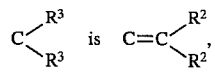

C=C=O, C=N—$R^2$ or C=O, or

is C=C, and $R^3$ may bond together with or without O or N atom to form a cyclic group; and $R^2$ is as defined above]. The above substituent $R^3$ is the same or different. Examples of the substituent represented by $R^3$ include —$R^2$, —$CO_2H$, —CN and the like Further, the substituent represented by $R^3$ may be those in which the same $R^3$ or two substituents $R^3$ on the adjacent carbon atom bond together to form a functional group, for example, those in which

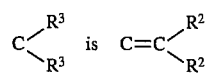

(methylene group), C=.=O (ketene group), C=N—$R^2$ (imino group) or C=O (carbonyl group), or

is C=C.

Further, the substituent $R^3$ and the other substituent $R^3$ may bond together with or without O or N atom to form a cyclic group. For example, the cyclic group is formally represented by bonding each radical group —R., which is formed by abstracting hydrogen radical from each atom on each $R^3$ to be bonded, together with or without O atom or N atom. Examples of the cyclic group include acid anhydride group (—COOCO—) of a structure wherein radical —COO.

formed by abstracting radical H. from —CO$_2$H group is bonded with radical —CO. formed by abstracting radical H. from —CHO; N-substituted imide group (—CONR$^1$CO—) of a structure wherein —CONR$^1$. is bonded with the above radical —CO.; unsaturated dicarbonyl group [—COC(R$^2$)=C(R$^2$)CO—] of a structure wherein —CO(R$^2$)=C(R$^2$). formed by abstracting radical H. from —COC(R$^2$)=C(R$^2$)H is bonded with the above radical —CO. and the like.

As the compound [XI], for example, there are maleic anhydride, N-methyl maleimide, N-phenyl maleimide, dimethyl fumarate, dimethyl maleate, dimethyl acetylenedicarboxylate, methyl propionate, methyl ethyl ketone, phenyl benzoyl acetylene ethyl-2-phenyl propionate, phenyl acetylene, allene, quinone, benzoquinone, tetracyanoethylene, tetracyanoquinone, diphenyl ketene and the like.

In the above reaction, Lewis acid may be used as a catalyst. Examples of the Lewis acid include zinc chloride, tin chloride, aluminum chloride, BF$_3$. (C$_2$H$_5$)$_2$O and the like. Further, the reaction may be conducted in the above inert solvent. The rection composition may be based on a stoichiometric ratio. For example, the reaction is conducted using 1 to 30 molar equivalent of the compound [VIII] based on the compound [IV] or IV]. The reaction is normally conducted by mixing with stirring at −20° to 200° C. Thereafter, if necessary, the solvent is distilled off and filtered, and then a normal refining operation (e.g. recrystallization, column chromatography, etc.) is conducted to obtain novel copounds [IX] to [X] of the present invention.

In particular, when the compound [XI] is used as the compound [VIII], novel compounds represented by the following formulas:

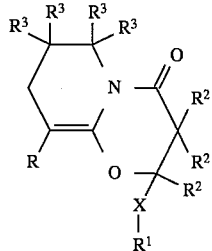

[wherein R, R$^1$, R$^2$, R$^3$ and X are as defined above], and

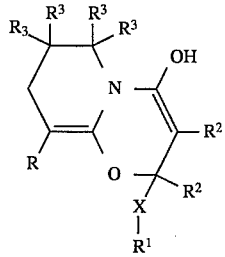

[wherein R, R$^1$, R$^2$, R$^3$ and X are as defined above] are obtained.

In the present invention, according to a novel method for employing whole conjugated system of an acylisocyanate group in the isocyanate compound [I], novel compounds [IV] to [VII] could be obtained and, further, the compounds [IX] to [V] (particularly, the compounds [IX'] to [X']) could be obtained. The heterocyclic compounds [IV] and [V] have conjugated double bond structures, as shown in the following formula:

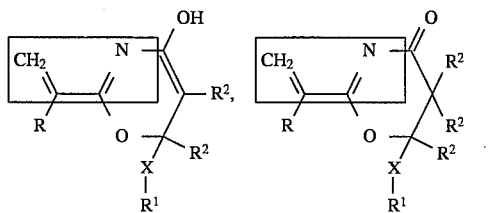

The above conjugated double bond structure has polymerization reactivity and, therefore, the heterocyclic compounds [IV] and [V] can be used for the production of a homopolymer or copolymer. For example, the compound is used for the modification of a synthetic fiber, synthetic resin, natural high polymer and the like after subjecting it to a graft polymerization. Further, the compound is used for the production of a varnish, coating, adhesive, plastic, elastomer and the like after polymerizing it as it is or polymerizing it with the other comohomer.

Further, the above conjugated double bond structure makes a cyclic addition reaction with various dienofiles to provide various heterocyclic compounds represented by novel compounds [IX'] to [X'] of the present invention. In these heterocyclic compounds, various functional groups can be introduced by varying dienophile, and various bioactivities may be expected from their molecular structures. Therefore, they become significant intermediates for synthetic raw materials in the fields of fine chemicals (e.g. medicines, pesticides, etc.).

As described above, novel heterocyclic compounds [IV] to [VII], [IX] and [X] have a wide variety of applications for industrial raw materials. Further, these heterocyclic compounds can be easily conducted with simple operation.

Further, the acylisocyanate compound [I] as a raw substance can be produced by reacting α-alkyl acrylamide with oxalyl halide. The reaction is normally conducted at a temperature of 0° to 100° C. under the presence of an inert solvent such as halgenated hydrocarbon. Further, in order to avoid an unnecessary polymerization of a terminal double bond, a polymerization inhibitor may be added to the reaction system. Examples of the polymerization inhibitor include hydroquinone, p-methoxyphenol, 2,6-di-t-butyl-4-methylphenol, 4-t-butyl catechol, bis-dihydroxybenzyl benzene, 2,2'-methylene-bis(6-t-butyl-3-methylphenol), 4,4'-butylidene-bis( 6-t-butyl-3-methylphenol), 4,4'-thio-bis(6-t-butyl- 3-methylphenol), p-nitrosophenol, diisopropyl xanthogensulfide, N-nitrosophenylhydroxyamine ammonium salt, 1,1-diphenyl-2-picrylhydrazyl, 1,3,5-triphenylfeldazyl, 2,6-di-t-butyl-α-( 3,5-di-t-butyl-4-oxo-2,5-cyclohexadiene-1-ylidene)-p-trioxy, 2,2,6,6,-tetramethyl-4-piperidone-1-oxyl, dithiobenzoyl sulfide, p,p'-ditolyl trisulfide, p,p'-ditolyl tetrasulfide, dibenzyl tetrasulfide, tetraethylthiuram sulfide and the like.

The following Examples further illustrate the present invention in detail but are not to be construed to limit the scope thereof.

EXAMPLES 1 TO 7

Preparation of Heterocyclic Compound [IV]

According to a composition shown in Table 1, methacryloyl isocyanate [I] was reacted with each compound [III'] under the reaction conditions shown in Table 1. After the reaction was completed, the deposited crystal was filtered off to obtain each heterocyclic compound [IV]. Yield and various physical properties of each heterocyclic compound [IV] are shown in Table 2.

TABLE 1

$$R^1X\diagdown_{R^2}C=CH\diagup^{R^{2'}} \quad [III']$$

| | Methacryloyl isocyanate [I] mg (mmol) | R¹X— | R²— | R²'— | mg (mmol) | Solvent | Reaction conditions Temperature | Time |
|---|---|---|---|---|---|---|---|---|
| Ex. 1 | 280 (2.5) | ⟨pyrrolidine⟩N— | Ph— | H— | 530 (3.1) | — | Room Temp. | 5 minutes |
| Ex. 2 | 500 (4.5) | | | | 850 (4.9) | ⟨benzene⟩ | Room Temp. | 3 hours |
| Ex. 3 | 1780 (16) | ⟨morpholine⟩O⟨⟩N— | Ph— | H— | 3020 (16) | CH₃CN | Room Temp. | 20 hours |
| Ex. 4 | 640 (5.8) | | | | 1100 (5.8) | CH₃CN | reacted at room temp. for 2 hours, followed by refluxing for 4 hours | |
| Ex. 5 | 2550 (23) | H₅C₂O— | H— | H— | 2160 (30) | CH₃CN | reacted at room temp. for 8 hours, followed by refluxing for 7 hours | |
| Ex. 6 | 2550 (23) | H₃CO— | H₃C— | H— | 2880 (40) | CH₃CN | reacted at room temp. for 48 hours, followed by at 50 to 60° C. for 9 hours | |
| Ex. 7 | 2550 (23) | | | | 1656 (23) | CH₃CN | reacted at room temp. for 5 hours, followed by at 50 to 55° C. for 10 hours with providing ultrasonic vibration | |

TABLE 2

Product [IV]:
$$\begin{array}{c} H_2C \\ \diagdown \\ H_3C \end{array} \diagup \begin{array}{c} OH \\ | \\ N \\ \| \\ \diagup \end{array} \begin{array}{c} R^{2'} \\ R^2 \\ R^1X \end{array}$$

| | Yield (%) | R¹X— | R²— | R²'— | Melting point (°C.) | IR (KBr, cm⁻¹) | ¹H-NMR (CDCl₃, δ) | MS (Mass spectrum) m/z (Relative intensity, %) |
|---|---|---|---|---|---|---|---|---|
| Ex. 1 | 34 | ⟨⟩N— | Ph— | H— | 178 ∫ 180 | — | — | — |
| Ex. 2 | 55 | | | | | | | |
| Ex. 3 | 53 | O⟨⟩N— | Ph— | H— | 144 ∫ 147 | — | — | — |
| Ex. 4 | 46 | | | | | | | |
| Ex. 5 | 24 | H₅C₂O— | H— | H— | 71 ∫ 72.5 | 3280 (OH), 1710 (C=N), 1620 (C=C) | 1.38(3H, t, J=7Hz), 2.00(3H, d, J=2Hz), 4.00(2H, q, J=7Hz), 5.57(1H, q, J=2Hz), 6.00(1H, S), 6.32(1H, d, J=12Hz), 9.65(1H, br.s) | 183 (M, 19), 72 (19), 71 (base peak) |
| Ex. 6 | 35 | H₃CO— | H₃C— | H— | 110 ∫ 113 | 3240 (OH) 1630 (C=N) | 2.00(3H, d, J=2Hz), 2.37(3H, S), 3.77 (3H, S), 5.55(1H, q, | 183 (M, 20) 99 (100) |
| Ex. 7 | 33 | | | | | | | |

TABLE 2-continued

Product [IV]:
(structure with H2C, H3C, N, OH, R2', O, R2, R1X substituents)

| Yield (%) | R1X— | R2— | R2'— | Melting point (°C.) | IR (KBr, cm⁻¹) | ¹H-NMR (CDCl₃, δ) | MS (Mass spectrum) m/z (Relative intensity, %) |
|---|---|---|---|---|---|---|---|
| | | | | | | J=2Hz), 5.88(1H, S), 6.55(1H, S), 8.63 (1H, br.s) | |

EXAMPLE 8

Production of Heterocyclic Compound [IX']

2-Isopropenyl-4-hydroxy-6-morpholino-6-phenyloxazine (0.88 g, 2.9 mmole), N-methylmaleimide (0.6 g, 5.4 mmol) and zinc chloride (41 mg) were added to xylene (10 ml) and the mixture was heated at reflux for 6 hours. After cooling in air, xylene was distilled off under reduced pressure and the residue was subjected to silica gel chromatography to obtain an adduct as a crystal having a melting point of 241° to 243° C. Various physical properties of the resulting adduct are as follows.

IR (KBr); 1770, 1700 (C=O) cm⁻¹

¹H-NMR (CDCl₃); δ=2.24–2.52 (4H, m, N(CH₂)₂), 2.60–3.12 (5H, m, CH₂×2, CH), 2.90 (3H, s, CH₃), 3.07 (3H, s, N-CH₃), 3.28–3.64 (5H, m, O(CH₂)₂, CH), 6.88–7.44 (5H, m, Ar-H)

Mass spectrum m/z (relative intensity, %) 411 (M⁺, 45), 300 (M⁺-N-methylmaleimide, 19), 299 (base peak)

Elemental analysis (%),
Calcd. for C₂₂H₂₅N₃O₅: C, 64.24; H, 6.08; N, 10.22
Found: C, 64.43; H, 6.15; N, 10.14

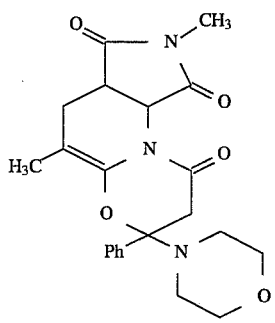

EXAMPLES 9 TO 14

Production of Heterocyclic Compounds [VII and [VII]

According to a composition shown in Table 3, methacryloyl isocyanate [I] was reacted with each compound [XIII] under the reaction conditions shown in Table 3. After the reaction was completed, the deposited crystal was filtered off to obtain heterocyclic compounds [VI] and [VII]. Various physical properties of each heterocyclic compound [VI] obtained in Examples 10 and 11 are shown below.

Heterocyclic compound [VI] of the Example 10:

IR (KBr); 3270, 3160 (NH), 1750, 1690 cm⁻¹ (C=O)

¹H-NMR (CDCl₃); δ=0.84–2.56 (14H, m, CH₂), 1.20 (3H, s, CH₃), 2.60–3.00 (4H, m, N(CH₂)₂), 8.40 (1H, brs, NH)

Mass spectrum m/z (relative intensity, %) 285 (M⁺, 68), 194 (100)

Heterocyclic compound [VI] of Example 11:

IR (KBr); 3222, 3106 (NH), 1734, 1709 cm⁻¹ (C=O)

¹H-NMR (CDCl₃); δ=0.83–2.83 (12H, m, 5,6,7,8-H, N(CH₂)₂), 1.25 (3H, s, CH₃), 2.00 (2H, s, 4-H), 3.17–4.00 (4H, m, O(CH₂)₂), 8.18 (1H, brs, NH)

Mass spectrum m/z (relative intensity, %) 278 (M⁺, 86), 193 (100)

TABLE 3

| | Example | | | | | |
|---|---|---|---|---|---|---|
| | 9 | 10 | 11 | 12 | 13 | 14 |
| Methacryloyl isocyanate[I] mg (mmol) | 1110 (10) | 1110 (10) | 1110 (10) | 1110 (10) | 1110 (10) | 1110 (10) |
| Compound [VIII] $-(CH_2)_n-$ | $-(CH_2)_n-$ | $-(CH_2)_3-$ | $-(CH_2)_4-$ | $-(CH_2)_4-$ | $-(CH_2)_5-$ | o-CH$_3$C$_6$H$_4$CH$_2$- |
| $R^1X-$ | morpholino | pyrrolidino | morpholino | morpholino | morpholino | pyrrolidino |
| Reaction conditions mg (mmol) | 1530 (10) | 1510 (10) | 1670 (10) | 1670 (10) | 1810 (10) | 1850 (10) |
| Solvent | CH$_3$CN | CH$_3$CN/C$_6$H$_6$ | CH$_3$CN | m-xylene | CH$_3$CN | CH$_3$CN |
| Room temp. (hour) | 12 | 18 | 12 | 3 | 1 | 1 |
| Reflux (hour) | 20 | 2 | 20 | 7 | 20 | 20 |
| Product Yield (%) | 5 | — | 15 | — | 11 | 2 |
| [VII] $-(CH_2)_n-$ | $-(CH_2)_n-$ | $-(CH_2)_3-$ | $-(CH_2)_4-$ | $-(CH_2)_4-$ | $-(CH_2)_5-$ | o-CH$_3$C$_6$H$_4$CH$_2$- |
| Melting point (°C.) | 188–190 | — | 163–164 | — | 140–143 | 192–195 |
| Product Yield (%) | — | 5 | 24 | 24 | — | — |
| [VI] $-(CH_2)_n-$ | $-(CH_2)_n-$ | $-(CH_2)_3-$ | $-(CH_2)_4-$ | $-(CH_2)_4-$ | $-(CH_2)_5-$ | o-CH$_3$C$_6$H$_4$CH$_2$- |
| $-XR^1$ | morpholino | pyrrolidino | morpholino | morpholino | morpholino | pyrrolidino |
| Melting point (°C.) | — | 227–228 | 205–207 | — | — | — |

EXAMPLE 15

Methacryloyl isocyanate (1.11 g, 10 mmol) and 1-morpholino-1-phenylpropene (2.03 g, 10 mmol) were stirred in acetonitrile at room temperature for 12 hours, followed by stirring under heating at reflux for 20 hours. The reaction mixture was subjected to a column chromatography to obtain a heterocyclic compound (7.8%).

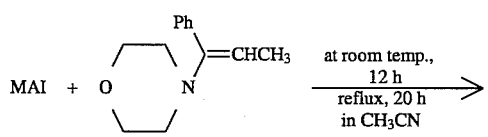

-continued

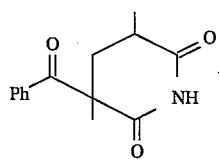

Melting point: 168°–170° C.

IR (KBr, cm$^{-1}$); 3188, 1707

$^1$H-NMR (CDCl$_3$, δ); 1.32 (3H, d), 1.66 (3H, s), 1.86 (1H, dd), 2.40(1H, dd), 2.80 (1H, ddd), 7.20–8.00 (5H, m), 8.66 (1H, bs)

What is claimed is:

1. A heterocyclic compound selected from the group consisting of the compounds IV to VII wherein the compounds IV to VII are represented by the formulas:

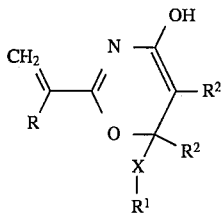   IV wherein R is a lower alkyl group; $R^1$ is an alkyl having 1 to 6 atoms, an aryl group having 6 to 10 carbon atoms, an aralkyl group having 7 to 8 carbon atoms, an alkenyl having 2 or 3 carbon atoms or an alkynyl having 2 or 3 carbon atoms; each $R^2$ is the same or different and respectively indicates —H, —$R^1$, or —$OR^1$, —$CONR_2^1$, —$CONHR^1$, —CHO, —$COR^1$, —$CO_2R^1$, —$NO_2$ or halogen atom, or $R^1$ and $R^2$ may not bond together;
X is

—O—, —S—, or

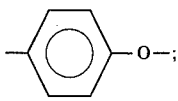

two substituents —$R^1$ on N atom is the same or different when X is

and they may bond together with O to form a six-membered ring with the oxygen in the 4 position to the ring N; and the above substituents $R^1$ and $R^2$ may be substituted with a substituent selected from the group consisting of an alkyl, alkenyl, aralkyl, alkynyl, aryl, cycloalkyl, alkoxy, halogen, acyl, ester, nitro, cyano, sulfide, sulfone, tertiary amino, and silicon,

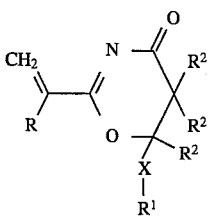   V wherein R, $R^1$, $R^2$ and X are as defined above,

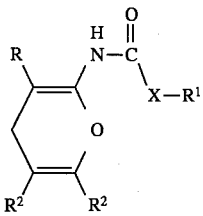   VI wherein R, $R^1$, $R^2$ and X are as defined above,

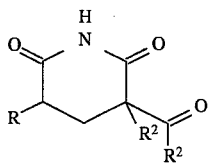   VII wherein R, and $R^2$ are as defined above.

2. The heterocyclic compound according to claim 1, wherein $R^1$ is a substituent selected from the group consisting of an alkyl, aryl and aralkyl group and $R^2$ is a substituent selected from the group consisting of hydrogen, an alkyl, aryl and aralkyl group.

3. A process for producing a heterocyclic compound selected from the group consisting of the compounds IV to VII represented by the following formulas:

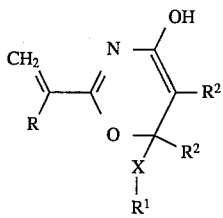   IV wherein R, $R^1$, $R^2$ and X are as defined below,

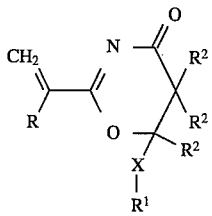   V wherein R, $R^1$, $R^2$ and X are as defined below,

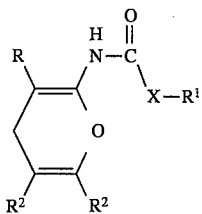   VI wherein R, $R^1$, $R^2$ and X are as defined below,

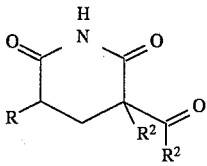   VII wherein R and $R^2$ are as defined below,
wherein R is a lower alkyl group, $R^1$ is an alkyl group having 1 to 6 carbon atoms, an aryl group having 6 to 10 carbon atoms, an aralkyl group having 7 to 8 carbon atoms, an alkenyl having 2 or 3 carbon atoms or alkynyl group having 2 or 3 carbon atoms; each $R^2$ is the same or different and respectively indicates —H, —$R^1$, or —$OR^1$, —$CONR_2^1$, —$CONHR^1$, —CHO, —$COR^1$, —$CO_2R^1$, —$NO_2$ or halogen atom, or $R^1$ and $R^2$ may bond together to form a cyclic group;
X is

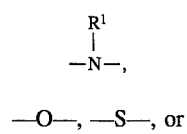

—O—, —S—, or

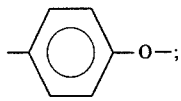

two substituents —R¹ on N atom is the same or different when X is

and they may bond together with or without O atom to form a cyclic group; and the above substituents R¹ and R² may be substituted, which process comprises reacting a compound represented by the formula:

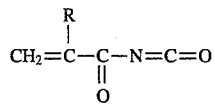  I with a compound represented by the formula:

A=B    II wherein A=B is a compound selected from the group consisting of vinyl ethers, enamines, vinyl thioethers, alkoxyalkynes, thioalkoxyalkynes, ynnamines, N-substituted maleimides, maleic anhydride, maleic acid and esters thereof, fumaric acid and esters thereof, acetylenemonocarboxylic acids and esters thereof, acetylenedicarboxylic acids and esters thereof, phenylacetylenes, acylated acetylenes, (moth)acrylic acid and esters thereof, (meth)acrylonitrile, quinones, cyanoethylenes, isocyanates, ketenes, ketenimines, carbodiimides, thioketenes, sulfinylimines, ketones, isocyanides, carbenes, allenes, isothiocyanates, sulfines, carbon bisulfide, sulfondiimides, azomethine compounds, nitriles, oxiranes, nitrons, nitrile oxides, thiiranes and azirines, and A=B may be substituted or have a cyclic structure.

4. The process for producing a heterocyclic compound according to claim 3, wherein the compound of the formula II is a compound represented by the formula:

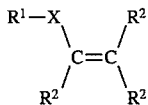  III wherein R¹ is an alkyl group having 1 to 6 carbon atoms, an aryl group having 6 to 10 carbon atoms, an aralkyl group having 1 to 8 carbon atoms, an alkenyl group having 2 or 3 carbon atoms or an alkynyl group having 2 or 3 carbon atoms; each R² is the same or different and respectively indicates —H, —R¹, —OR¹, —CONHR₂¹, —CONHR¹, —CHO, —COR¹, —CO₂R¹, —NO₂, or halogen atom, or R¹ and R² may bond together to form a cyclic group; X is

—O—, —S—, or

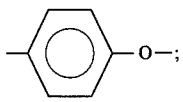

two substituents —R¹ on N atom is the same or different when X is

and they may bond together with or without O atom to form a cyclic group; and the above substituents R¹ and R² may be substituted, and the heterocyclic compound is a compound selected from the group consisting of the compounds IV to VII represented by the following formulas:

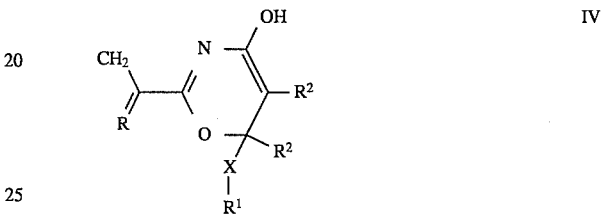  IV wherein R is a lower alkyl, R¹, R² and X are as defined above

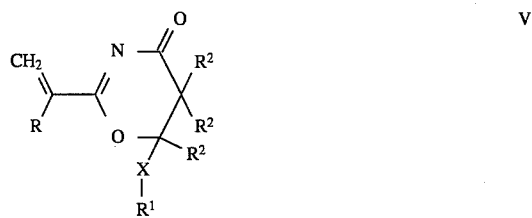  V wherein R, R¹, R² and X are as defined above

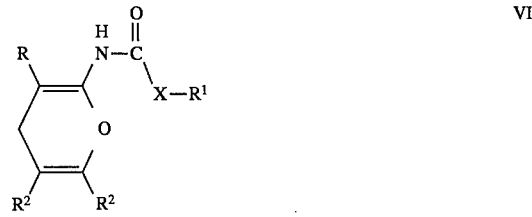  VI wherein R, R¹, R² and X are as defined above, and

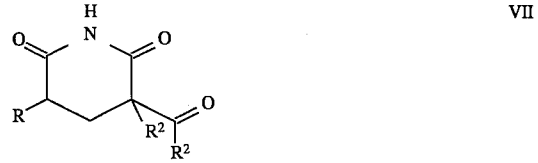  VII wherein R and R² are as defined above.

5. The process for producing a heterocyclic compound according to claim 3, wherein R¹ is a substituent selected from the group consisting of an alkyl group having 1 to 6 carbon atoms, an aryl group having 6 to 10 carbon atoms and an aralkyl group having 7 to 8 carbon atoms and R² is a substituent selected from the group consisting of an alkyl group having 1 to 6 carbon atoms, an aryl group having 6 to 10 carbon atoms and an aralkyl group having 7 to 8 carbon atoms.

* * * * *